United States Patent [19]
Okada et al.

[11] Patent Number: 5,892,026
[45] Date of Patent: *Apr. 6, 1999

[54] HIGH TREHALOSE CONTENT SYRUP

[75] Inventors: Katsuhide Okada; Takashi Shibuya; Toshio Miyake, all of Okayama, Japan

[73] Assignee: Kabushiki Kaisha Hayashibara Seibutsu Kagaku Kenkyujo

[ * ] Notice: This patent issued on a continued prosecution application filed under 37 CFR 1.53(d), and is subject to the twenty year patent term provisions of 35 U.S.C. 154(a)(2).

[21] Appl. No.: 630,492

[22] Filed: Apr. 10, 1996

[30] Foreign Application Priority Data

Apr. 12, 1995 [JP] Japan ................ 7-110291

[51] Int. Cl.$^6$ .......... C12P 19/12; C13K 13/00; C07H 3/04; A23G 1/09
[52] U.S. Cl. ............ 536/123.13; 536/124; 536/127; 514/53; 426/422; 426/658; 426/660
[58] Field of Search ............... 536/123.13, 127, 536/124; 514/53; 426/658, 660, 422

[56] References Cited

FOREIGN PATENT DOCUMENTS

| | | |
|---|---|---|
| 0 606 753 A2 | 12/1993 | European Pat. Off. . |
| 0 628 630 A2 | 6/1994 | European Pat. Off. . |
| 0704531 | 3/1996 | European Pat. Off. . |
| 58-216695 | 12/1983 | Japan . |
| 63-240757 | 6/1988 | Japan . |
| 63-240758 | 6/1988 | Japan . |
| 5-349216 | 12/1993 | Japan . |
| 6-79291 | 3/1994 | Japan . |

OTHER PUBLICATIONS

Database WPI Section Ch, Week 8750, Apr. 27, 1988, Derwent Publications Ltd., London, GB; Class D13, AN 87–352,938, Y. Iijima et al.: "Preparation of Fondant–Like Sugar Candy from Palatinose." & JP–A–62 257,346 (Lotte Co., Ltd.), Nov. 9, 1987 *Abstract* .

Shoichi Kobayashi, Current Staus of Starch Application Development and Related Problems, No. 88, pp. 67–72, Aug. 1992.

Hoelzle et al, Increased Accumulation of Trehalose in Rhizobia Cultured Under 1% Oxygen, Applied and Environmental Microbiology, vol. 56, No. 10, pp. 3213–3215, Oct. 1990.

Wolfrom et al, Advances in Carbohydrate Chemistry, Academic Press, vol. 18, pp. 201–225, 1963.

Denpun–Kagaku Handbook (Handbook of Starch Science), edited by J. Nikuni, Tokyo, Japan, pp. 456–459, 1984.

*Primary Examiner*—Francisco Prats
*Attorney, Agent, or Firm*—Browdy and Neimark

[57] ABSTRACT

Disclosed is a non- or substantially non-crystalline high trehalose content syrup, which is supersaturated in trehalose and which further comprises another dissolved saccharide in an amount at least as much as the amount of trehalose. The saccharide acts to prevent crystallization of trehalose. The saccharide may be a reducing monosaccharide, a non-reducing monosaccharide or an oligosaccharide. The supersaturated trehalose solutions are free from bacterial contamination even at ambient temperature.

16 Claims, No Drawings

HIGH TREHALOSE CONTENT SYRUP

BACKGROUND OF THE INVENTION

1. Field of the Invention

The present invention relates to a stable syrup which contains the highest possible amount of trehalose, more particularly, to a high trehalose content syrup in which trehalose is dissolved in an amount that exceeds its saturation concentration in water along with other saccharide(s) and which syrup is free of or substantially free of crystallization of trehalose, and to uses thereof. The present invention also relates to a method for preventing the crystallization of trehalose in a high trehalose content syrup, an agent which contains as an effective ingredient a reducing and/or a non-reducing saccharide for preventing the crystallization of trehalose, and a method for preventing the crystallization of trehalose characterized by a step of dissolving the agent in a high trehalose content syrup.

2. Description of the Prior Art

Trehalose, α,α-trehalose, has long been known as a non-reducing saccharide which is composed of glucose units. It is described in "Advances in Carbohydrate Chemistry", published by Academic Press, USA, Vol.18, pp.201–225 (1963) and in "Applied and Environmental Microbiology", Vol.56, pp.3,213–3,215 (1990) that trehalose is widely distributed in microorganisms, mushrooms and insects in an extremely small amount. Non-reducing saccharides like trehalose neither cause the amino carbonyl reaction with amino acid containing substances such as amino acids and proteins nor deteriorate amino acid containing substances, and therefore they can be used and processed with these substances without causing unsatisfiable browning reaction and deterioration. As a result, there was the expectation that the production of trehalose would be established on an industrial scale.

In conventional preparations of trehalose, microorganisms are utilized as disclosed in Japanese Patent Laid-Open No.154,485/75, and as disclosed in Japanese Patent Laid-Open No.216,695/83, maltose is converted into trehalose by using maltose- and trehalose-phosphorylases in combination. However, the former is not suitable for the industrial production of trehalose because the amount of trehalose in microorganisms as a starting material is usually less than 15 w/w % (the working "w/w %" will be abbreviated as "%" in the present specification, unless specified otherwise), on a dry solid basis (d.s.b.), and the extraction and purification steps are complicated. The later has the following demerits: (i) Trehalose is formed via glucose-1-phosphate so that maltose as a substrate could not be used at a relatively-high concentration; (ii) The enzymatic reaction systems of these phosphorylases are reversible reactions, and this renders the yield of the objective trehalose relatively low; and (iii) It is substantially difficult to keep the reaction systems stable and to continue these enzymatic reactions smoothly. Thus, it has not yet been actually used as an industrial-scale preparation.

As regards the preparation of trehalose, it is reported in the column titled "Oligosaccharides" in the chapter titled "Current Status of Starch Application Development and Related Problems" in "Food Chemicals", No.88, pp.67–72 (August, 1992) that "In spite of a wide applicability of trehalose, an enzymatic preparation thereof via a direct saccharide-transfer reaction or a hydrolytic reaction has been recognized to be scientifically almost impossible." Thus, an enzymatic preparation of trehalose using starch as a material has been deemed to be scientifically impossible.

It is known that partial starch hydrolysates such as liquefied starches, cyclodextrins and maltooligosaccharides which are prepared from starch a material usually have a reducing end-group as an end unit. These partial starch hydrolysates are referred to as "reducing partial starch hydrolysates" in the present specification. The reducing power of reducing partial starch hydrolysates is generally expressed by "DE" (dextrose equivalent), based on a dry solid (d.s.b). It is known that, among reducing partial starch hydrolysates, those with a relatively-high DE have generally a relatively-lower molecular weight and viscosity and a relatively-higher sweetening power and reactivity, and readily react with substances having amino groups such as amino acids and proteins to cause undesirable browning, smell and quality deterioration.

These properties of reducing partial starch hydrolysates vary depending on their DE values, and the relationship between reducing partial starch hydrolysates and their DE is very important. It has been even believed in this field that it is impossible to break off the relationship.

To solve this problem, the present applicant disclosed in Japanese Patent Application No.349,216/93 that a novel non-reducing saccharide-forming enzyme which forms non-reducing saccharides, having a trehalose structure as an end unit, from one or more reducing partial starch hydrolysates selected from those with a DE of at least 3 (the enzyme will be referred to as "non-reducing saccharide-forming enzyme, throughout the present specification"). The applicant established a process for producing non-reducing saccharides having a degree of glucose polymerization of at least 3 and having a trehalose structure as an end unit, and a process for producing trehalose from these saccharides by using the non-reducing saccharide-forming enzyme.

The present applicant also disclosed in Japanese Patent Application No.79,291/94 that a novel trehalose-releasing enzyme which specifically hydrolyses the linkage between trehalose and other molecules in non-reducing saccharides having a degree of glucose polymerization of at least 3 and having a trehalose structure as an end unit (the enzyme will be referred to as "trehalose-releasing enzyme", throughout the present specification), and established a process for producing trehalose with an increased yield by using the above two novel enzymes in combination. The present applicant further disclosed in Japanese Patent Application No.144,092/94 that a maltose-trehalose converting enzyme which directly converts maltose into trehalose, and established a process for producing trehalose in a relative-high yield from maltose produced from reducing partial starch hydrolysates.

During studying the uses of trehalose, the present inventors noticed that in addition to hydrous- and anhydrous-crystalline trehaloses, the tankage, trucking and pumping transportation of high trehalose content syrups are greatly required. However, the water solubility of trehalose is relatively low, and unsaturated trehalose solutions are susceptible to bacterial contamination because of their relatively low concentration, while supersaturated trehalose solutions are considerably poor in stability at ambient temperature and susceptible to crystallization and precipitation of hydrous crystalline trehalose, readily resulting in loss of their satisfactory homogeneous free-flowing ability and in a serious damage when stored in tanks or transported by pumps. Therefore, stable trehalose syrups with the highest possible content of trehalose are strongly required.

SUMMARY OF THE INVENTION

The present invention provides a stable high trehalose content syrup which has the highest possible amount of trehalose and is free of or substantially free of crystallization and bacterial contamination even at ambient temperature, and provides its uses and a method for preventing the crystallization of trehalose in high trehalose content syrups.

To overcome the present object, the present inventors aimed to study a method for preventing the crystallization of trehalose and energetically studied to establish a stable trehalose syrup in which trehalose is dissolved in the highest possible amount at ambient temperature. As a result, they found that the following syrups are satisfactorily stable even at ambient temperature and they fulfill the present object: Syrups prepared by dissolving trehalose in water in an amount that exceeds its saturation concentration in water together with other saccharide(s), preferably, trehalose syrups prepared by dissolving trehalose in water in an amount that exceeds its saturation concentration in water and together with other saccharide(s) in an amount which is at least as much as the same amount of trehalose dissolved, more preferably, high trehalose content syrups which contain 18.5–25.0 w/w % trehalose, 25.0–35.0 w/w % water, and 40.0–56.5 w/w % of other saccharide(s) with respect to the syrups. Thus, the present inventors accomplished this invention.

DETAILED DESCRIPTION OF THE INVENTION

The high trehalose content syrups, in which trehalose is dissolved in an amount over its saturation concentration in water and together with other saccharide(s), that are suitably used in the present invention are those in which 18.5–25.0 w/w % trehalose is dissolved and other saccharide(s) in an amount which is at least as much as the amount of the trehalose dissolved, and which are free of or substantially free of crystallization. Any method can be used in the present invention as long as it produces the above syrups. For example, such syrups can be produced by dissolving a prescribed amount of trehalose in water under heating conditions, and dissolving other saccharide(s) in an amount which is at least as much as the amount of the trehalose dissolved, or produced by mixing trehalose-rich solutions, prepared by dissolving trehalose in water under heating conditions, with other saccharide-rich solutions to meet to their final uses.

Any process for producing trehalose can be used in the present invention. In general, low-cost crude trehalose preparations which contain other saccharides can be more suitably used than commercially available high-cost and high-purity trehalose preparations. Examples of the crude trehalose preparations are trehalose-containing syrups or mother liquors prepared by concentrating and crystallizing the syrups into massecuites containing hydrous crystalline trehalose, and separating the massecuites. These syrups and mother liquors can be obtained by allowing a non-reducing saccharide-forming enzyme and a trehalose-releasing enzyme to act on reducing partial starch hydrolysates as disclosed in Japanese Patent Application Nos.349,216/93, 79,291/94 and 165,815/94, or by allowing a maltose/trehalose converting enzyme to act on reducing partial starch hydrolysates as disclosed in Japanese Patent Application No.144,092/94. These trehalose-containing solutions generally contain about 40–80 w/w % trehalose, d.s.b., and can be suitably used in the present invention as material syrups.

The other saccharides preferably used in the present invention include those which readily dissolve in water and prevent the crystallization of trehalose. For example, reducing saccharides and oligosaccharides such as glucose, fructose, maltose, isomaltose, maltotriose, isomaltotriose, panose, maltotetraose and maltopenatose, and non-reducing saccharides and oligosaccharides such as sorbitol, maltitol, isomaltitol, lactitol, panitol, neotrehalose, sucrose, raffinose, erlose, lactosucrose, α-glycosyltrehalose, α-glycosyl α-glycoside, and α-glycosyl sucrose can be selectively used. These saccharides can be suitably used as an effective ingredient for agents to prevent the crystallization of trehalose, and particularly those which consist of two or more of reducing and/or non-reducing saccharides, composed of not higher than five monosaccharide units, can be selectively used.

In the case of using as a sweetener the high trehalose content syrups according to the present invention, saccharides which are composed of not higher than five monosaccharide units, preferably, not higher than four monosaccharide units, and have a relatively-low molecular weight and a relatively high sweetening power can be suitably used as an agent for preventing the crystallization of trehalose. For example, commercially available saccharide syrups such as maltose rich syrups, maltotetraose rich syrups, panose rich syrups, glycosyl sucrose, lactosucrose rich syrups, and maltitol rich syrups can be satisfactorily used. To increase the crystallization inhibitory effect on trehalose, one or more saccharides other than trehalose should coexist with trehalose in an amount which is at least as much as the amount of trehalose or, preferably, at least 1.5-fold times the amount of trehalose. If necessary, one or more organic acids, minerals, amino acids and peptides can be incorporated into the high trehalose content syrups in addition to the agents for preventing the crystallization of trehalose to increase their effect.

The high trehalose content syrups used in the present invention can be prepared directly from starch or maltose. The direct production of trehalose from starch includes a method below: Prepare a starch suspension with a concentration of at least 10 w/w %, d.s.b., according to the method as disclosed in Japanese Patent Application No.165,815/94 applied for by the present applicant, allow an acid or α-amylase to act on the starch suspension to obtain a liquefied starch solution with a DE of 15 or higher, allow a starch debranching enzyme, non-reducing saccharide-forming enzyme, a trehalose-releasing enzyme to act on the liquefied starch solution to form 28–33 w/w % trehalose, d.s.b., and allow one or more enzymes selected from α-amylase, β-amylase, glucoamylase, and cyclomaltodextrin glucanotransferase to act on the resulting trehalose solution. Heat the resulting mixture to inactivate the remaining enzymes in a conventional manner, decolor the mixture with an activated charcoal, desalt and purify the decolored mixture on ion-exchange resins (H- and OH-form), concentrate the purified mixture, and collect a high trehalose content syrup which contains 18.5–25.0 w/w % trehalose, 25.0–35.0 w/w % water, and 40.0–56.5 w/w % of other saccharides such as maltose, glucose, etc., with respect to the syrup.

The direct production of trehalose from maltose includes a method below: According to the method as disclosed in Japanese Patent Application No.144,092/94 applied for by the present applicant, a maltose/trehalose converting enzyme is allowed to act on a saccharide solution rich in maltose to form 28–33 w/w % trehalose, d.s.b., followed by purifying the saccharide solution in a conventional manner, concentrating the purified solution and collecting the concentrated solution containing 18.5–25.0 w/w % trehalose, 25.0–35.0 w/w % water, and 40.0–56.5 w/w % of other saccharides such as maltose, etc., with respect to the concentrated solution.

The high trehalose content syrups thus obtained are readily handleable and free of or substantially free of crystallization even in winter season with a temperature of 10° C. or lower. The syrups have a lower DE than those of conventional starch sugars, preferably, a DE of less than 50, and can be suitably used as syrups with a relatively low viscosity and high sweetening power in food products, cosmetics and pharmaceuticals. The present high trehalose content syrups can be concentrated into high-quality hard candies without crystallization of trehalose. The present syrups have properties of an osmosis-controlling activity, filler-imparting activity, gloss-imparting activity, moisture-retaining activity, viscosity-imparting activity, crystallization-preventing activity for other saccharides, substantial non-fermentability, and retrogradation-preventing activity.

The present syrups can be satisfactorily used as a sweetener, taste-improving agent, quality improving agent, stabilizer, and filler in a variety of compositions such as food products, feeds, pet foods, cosmetics and pharmaceuticals.

The present syrups in themselves can be used as a seasoning for sweetening and, if necessary, can be used with adequate amounts of one or more other sweeteners, for example, powdered syrup, glucose, maltose, sucrose, isomerized sugar, honey, maple sugar, isomaltooligosaccharide, galactooligosaccharide, fructooligosaccharide, lactosucrose, sorbitol, maltitol, lactitol, dihydrochalcone, stevioside, α-glycosyl stevioside, rebaudioside, glycyrrhizin, L-aspartyl L-phenylalanine methyl ester, saccharin, glycine and alanine; and/or a filler such as dextrin, starch and lactose.

If necessary, the present syrup can be suitably used together with hydrous crystalline trehalose to improve products containing hydrous crystalline trehalose. The syrup can be incorporated into products such as an icing, soft candy, and bonbon which contain hydrous crystalline trehalose in an amount of less than the amount of the hydrous crystalline trehalose, preferably, less than 50% of the trehalose to impart an adequate humidity, moldability, and adhesiveness of the final products and to keep the initial high quality of the products for a relatively long period of time.

The present syrups well harmonize with other materials having sour-, acid-, bitter-, astringent- and delicious-tastes, and have a relatively-high acid and heat tolerance. Thus, they can be favorably used in food products in general as a sweetener, taste-improving agent or quality-improving agent.

The present syrups can be used in seasonings such as an amino acid, peptide, soy sauce, powdered soy sauce, "miso", "funmatsu-miso" (a powdered miso), "moromi" (a refined sake), "hishio" (a refined soy sauce), "furikake" (a seasoned fish meal), mayonnaise, dressing, vinegar, "sanbai-zu" (a sauce of sugar, soy sauce and vinegar), "funmatsu-sushi-su" (powdered vinegar for sushi), "chuka-no-moto" (an instant mix for Chinese dish), "tentsuyu" (a sauce for Japanese deep-fat fried food), "mentsuyu" (a sauce for Japanese vermicelli), sauce, catsup, "yakiniku-no-tare" (a sauce for Japanese grilled meat), curry roux, instant stew mix, instant soup mix, "dashi-no-moto" (an instant stock mix), nucleic acid condiments, mixed seasoning, "mirin" (a sweet sake), "shin-mirin" (a synthetic mirin), table syrup and coffee syrup.

The present syrups can be also used for sweetening "wagashi" (Japanese cakes) such as "senbei" (a rice cracker), "arare-mochi" (a rice-cake cube), "okoshi" (a millet-and-rice cake), "mochi" (a rice paste), "manju" (a bun with a bean-jam), "uiro" (a sweet rice jelly), "an" (a beam jam), "yokan" (a sweet jelly of beans), "mizu-yoken" (a soft adzuki-bean jelly), "kingyoku" (a kind of yokan), jelly, pao de Castella and "amedama" (a Japanese toffee); confectioneries such as bun, biscuit, cracker, cookie, pie, pudding, butter cream, custard cream, cream puff, waffle, sponge cake, doughnut, chocolate, chewing gum, caramel and candy; frozen desserts such as ice cream and sherbet; syrups such as "kajitsu-no-syrup-zuke" (a preserved fruit) and "korimitsu" (a sugar syrup for shaved ice); pastes such as flour paste, peanut paste, fruit paste and spread; processed fruits and vegetable such as jam, marmalade, "syrup-zuke" (fruit pickles) and "toka" (conserves); pickles and pickled products such as "fukujin-zuke" (red colored radish pickles), "bettara-zuke" (a kind of whole fresh radish pickles), "senmai-zuke" (a kind of sliced fresh radish pickles) and "rakkyo-zuke" (pickled shallots); premixes for pickles and pickled products such as "takuan-zuke-no-moto" (a premix for pickled radish) and "hakusai-zuke-no-moto" (a premix for fresh white rape pickles); meat products such as ham and sausage; products of fish meat such as fish ham, fish sausage, "kamaboko" (a steamed fish paste), "chikuwa" (a kind of fish paste) and "tenpura" (a Japanese deep-fat fried fish paste); "chinmi" (relish) such as "uni-no-shiokara" (salted guts of sea urchin), "ika-no-shiokara" (salted guts of squid), "su-konbu" (processed tangle), "saki-surume" (dried squid strips) and "fugu-no-mirin-boshi" (a dried mirin-seasoned swellfish); "tsukudani" (foods boiled down in soy sauce) such as those of laver, edible wild plants, dried squid, fish and shellfish; daily dishes such as "nimame" (cooked beans), potato salad and "konbu-maki" (a tangle roll); milk products; canned and bottled products such as those of meat, fish meat, fruit and vegetable; alcoholic beverages such as synthetic sake, wine and liquors; soft drinks such as coffee, tea, cocoa, juice, carbonated beverage, sour milk beverage and beverage containing a lactic acid bacterium; instant food products such as instant pudding mix, instant hot cake mix and "sokuseki-shiruko" (an instant mix of adzuki-beam soup with rice cake) and instant soup mix; and beverages such as baby foods, foods for therapy, and beverages supplemented with nutrition; as well as for improving the tastes and qualities of the aforementioned food products.

The present syrups can be also used in feeds and pet foods for animals such as domestic animals, poultry, honey bees, silk worms and fishes to improve their taste preferences, and can be used as a sweetener, taste-improving agent, quality-improving agent or stabilizer in other products in a paste or a liquid form such as tobaccos, cigarettes, dentifrices, rouges, chapped lips, internal medicines, tablets, troches, cod liver oils in the form of a drop, cachous, oral refrigerants, gargles, cosmetics and pharmaceuticals.

The present syrups can be used as a quality-improving agent and stabilizer for biologically active substances susceptible to loss of their effective ingredients and activities, and used in health foods and pharmaceutical compositions in the form of a liquid, paste or solid, containing the biologically active substances. Examples of these biologically active substances are thiamine, riboflavin, L-ascorbic acid, cod liver oil, carotenoid, ergosterol and tocopherol; enzymes such as lipase, elastase, urokinase, protease, β-amylase, isoamylase, glucanase and lactase; extracts such as ginseng extract, snapping turtle extract, chlorella extract, aloe extract and propolis extract; viable microorganisms such as viruses, lactic acid bacteria and yeasts; and other biologically active substances such as royal jelly. By using the present syrups, the above biologically active substances are readily prepared into health foods and pharmaceuticals with a satisfactorily-high stability and quality without fear of losing or inactivating their effective ingredients and activities.

As is described above, the methods to incorporate the present syrups into the above compositions include conventional ones which incorporate the syrups before completion of the final products: For example, mixing, kneading, dissolving, melting, soaking, permeating, sprinkling, applying, coating, spraying, injecting and solidifying can be selectively used. The syrups are usually incorporated into the compositions in an amount of at least 0.5%, preferably, at least one %, d.s.b.

The following experiments explain the present invention in more detail:

EXPERIMENT 1

Influence of Ambient Temperature on Water Solubility of Trehalose

The water solubility of trehalose at ambient temperature was studied by placing into a glass beaker 10 parts by weight of water and 20 parts by weight of hydrous crystalline trehalose, incubating the mixture under stirring conditions at 10°, 15°, 20°, 25°, 30° or 40° C. for 24 hours in an incubator, filtering the resulting mixture, measuring the trehalose concentration of the filtrate, and determining the water solubility of trehalose in an anhydrous form in 100 g water at each temperature. The results were in Table 1.

TABLE 1

| Temperature (°C.) | 10 | 15 | 20 | 25 | 30 | 40 |
|---|---|---|---|---|---|---|
| A | 55.3 | 61.8 | 68.9 | 77.3 | 86.6 | 109.2 |
| B | 35.6 | 38.2 | 40.8 | 43.6 | 46.4 | 52.2 |

Note:
In Table 1, the symbols "A" and "B" mean "trehalose content (g) dissolved in 100 g water" and "trehalose concentration (w/w %)", respectively.

The results in Table 1 concluded that trehalose dissolves in water in a relatively low concentration and readily crystallizes at ambient temperature.

EXPERIMENT 2

Influence of Reducing Saccharide on the Crystallization Inhibitory Effect on Trehalose at Ambient Temperature Trehalose was dissolved in water by heating into an saturated solution at 15° C., and a reducing saccharide as an additional saccharide was dissolved in the saturated solution. The mixture was allowed to stand at a relatively low temperature for evaluating the crystallization inhibitory effect on trehalose. The results of Experiment 1 indicate that 18.5 parts by weight of trehalose saturates 30 parts by weight of water at 15° C. Based on this, a test solution was as shown in Table 2 prepared by placing into a glass beaker 30 parts by weight of water and 18.5 parts by weight of trehalose together with different amounts of glucose, maltose, maltotriose or maltotetraose, dissolving each saccharide in water under heating conditions, allowing to stand the resulting each solution at 5°, 10° or 15° C. in an incubator for a week, observing macroscopically the formation of trehalose crystal in each solution, and evaluating the crystallization inhibitory effect on trehalose by these saccharides. The results were in Table 2.

TABLE 2

| Composition (part by weight) | | | | | | | | | | | |
|---|---|---|---|---|---|---|---|---|---|---|---|
| Water | 30 | 30 | 30 | 30 | 30 | 30 | 30 | 30 | 30 | 30 | 30 |
| Trehalose | 18.5 | 18.5 | 18.5 | 18.5 | 18.5 | 18.5 | 18.5 | 18.5 | 18.5 | 18.5 | 18.5 |
| Glucose | 0 | 5 | 10 | 35 | 51.5 | 0 | 0 | 0 | 0 | 0 | 0 |
| Maltose | 0 | 0 | 0 | 0 | 0 | 5 | 10 | 35 | 51.5 | 0 | 0 |
| Maltotriose | 0 | 0 | 0 | 0 | 0 | 0 | 0 | 0 | 0 | 5 | 10 |
| Maltotetraose | 0 | 0 | 0 | 0 | 0 | 0 | 0 | 0 | 0 | 0 | 0 |
| Temperature (°C.) | | | | | | | | | | | |
| 5 | + | + | + | + | + | + | + | + | + | + | + |
| 10 | + | + | + | − | − | + | + | − | − | + | + |
| 15 | − | − | − | − | − | − | − | − | − | − | − |

| Composition (part by weight) | | | | | | | | | | | |
|---|---|---|---|---|---|---|---|---|---|---|---|
| Water | 30 | 30 | 30 | 30 | 30 | 30 | 30 | 30 | 30 | 30 | 30 |
| Trehalose | 18.5 | 18.5 | 18.5 | 18.5 | 18.5 | 18.5 | 18.5 | 18.5 | 18.5 | 18.5 | 18.5 |
| Glucose | 0 | 0 | 0 | 0 | 0 | 0 | 25.0 | 25.0 | 0 | 12.5 | 12.5 |
| Maltose | 0 | 0 | 0 | 0 | 0 | 0 | 26.5 | 0 | 25.0 | 12.5 | 12.5 |
| Maltotriose | 35 | 51.5 | 0 | 0 | 0 | 0 | 0 | 26.5 | 0 | 0 | 12.5 |
| Maltotetraose | 0 | 0 | 5 | 10 | 35 | 51.5 | 0 | 0 | 26.5 | 26.5 | 14.0 |
| Temperature (°C.) | | | | | | | | | | | |
| 5 | + | + | + | + | + | + | − | − | − | − | − |
| 10 | − | − | + | + | − | − | − | − | − | − | − |
| 15 | − | − | − | − | − | − | − | − | − | − | − |

Note:
In Table 2, the symbols "+" and "−" mean "crystallized" and "not crystallized", respectively.

As is evident from the results Table 2, it was revealed that the crystallization of trehalose in a 18.5 w/w % trehalose syrup, in which trehalose is dissolved in an amount that exceeds its saturation concentration in water, is prevented by dissolving a reducing saccharide in an amount which is at least as much as the amount of trehalose or, preferably, in an amount at least 1.5-fold times the amount of trehalose, and the crystallization inhibitory effect on trehalose is increased, i.e. trehalose does not crystallize even at 50° C. when two or more of reducing saccharides are dissolved in high trehalose content syrups.

EXPERIMENT 3

Influence of Non-Reducing Saccharide on the Crystallization Inhibitory Effect on Trehalose at Ambient Temperature The crystallization inhibitory effect on trehalose was studied by dissolving trehalose in water under heating conditions into a saturated solution at 25° C., dissolving other saccharide(s) in the solution, and allowing the resulting solution to stand at a relatively low temperature. The results of Experiment 1 indicate that 23.2 parts by weight of trehalose saturates 30 parts by weight of water at 25° C. Based on this, a test solution was as shown in Table 3 prepared by placing into a glass beaker 30 parts by weight of water and 23.2 parts by weight of trehalose together with a different amounts of sorbitol, maltitol, maltotriitol or sucrose as a non-reducing saccharide, dissolving each saccharide in water by heating, allowing to stand each solution at 10°, 20° or 25° C. in an incubator for a week, observing macroscopically the formation of trehalose crystal in each solution, and evaluating the crystallization inhibitory effect on trehalose by these non-reducing saccharides. The results were in Table 3.

As is evident from the results in Table 3, it was revealed that the crystallization of trehalose in a 23.2 w/w % trehalose syrup, in which trehalose is dissolved in an amount that exceeds its saturation concentration in water, is prevented by dissolving a non-reducing saccharide in the same amount or higher as the amount of trehalose, and the crystallization inhibitory effect on trehalose is increased, i.e. trehalose does not crystallize even at 10° C. when two or more of non-reducing saccharides are dissolved in high trehalose content syrups.

EXPERIMENT 4

Influence of Water on Bacterial Contamination of High Trehalose Content Syrup at Ambient Temperature By using aqueous trehalose solutions and high trehalose content syrups containing trehalose and other saccharides, the influence of water on the bacterial contamination and on the crystallization of trehalose was studied. The aqueous trehalose solutions as test solutions were prepared by dissolving 23.2 parts by weight of trehalose and a variety parts by weight of water as shown in Table 4, and the high trehalose content syrups were prepared by dissolving by heating 23.2 parts by weight of trehalose, 10 parts by weight of glucose, 16.8 parts by weight of maltose, 10 parts by weight of maltitol, and 10 parts by weight of sucrose in a variety parts by weight of water. Each solution or syrup was placed in a glass beaker, and allowed to stand at 15° C. for 2 months, followed by observing macroscopically the bacterial contamination in each solution or syrup and on the liquid surface, and observing the formation of trehalose crystal. The results were in Table 4.

TABLE 3

| Composition (part by weight) | | | | | | | | | | | | | | | | | | |
|---|---|---|---|---|---|---|---|---|---|---|---|---|---|---|---|---|---|---|
| Water | 30 | 30 | 30 | 30 | 30 | 30 | 30 | 30 | 30 | 30 | 30 | 30 | 30 | 30 | 30 | 30 | 30 | 30 |
| Trehalose | 23.2 | 23.2 | 23.2 | 23.2 | 23.2 | 23.2 | 23.2 | 23.2 | 23.2 | 23.2 | 23.2 | 23.2 | 23.2 | 23.2 | 23.2 | 23.2 | 23.2 | 23.2 |
| Sorbitol | 0 | 5 | 10 | 46.8 | 0 | 0 | 0 | 0 | 0 | 0 | 0 | 0 | 0 | 20 | 20 | 0 | 10 | 10 |
| Maltitol | 0 | 0 | 0 | 0 | 5 | 10 | 46.8 | 0 | 0 | 0 | 0 | 0 | 0 | 26.8 | 0 | 20 | 10 | 10 |
| Maltottriitol | 0 | 0 | 0 | 0 | 0 | 0 | 0 | 5 | 10 | 46.8 | 0 | 0 | 0 | 0 | 26.8 | 0 | 0 | 16.8 |
| Sucrose | 0 | 0 | 0 | 0 | 0 | 0 | 0 | 0 | 0 | 0 | 5 | 10 | 46.8 | 0 | 0 | 26.8 | 26.8 | 10 |
| Temperature (°C.) | | | | | | | | | | | | | | | | | | |
| 10 | + | + | + | + | + | + | + | + | + | + | + | + | + | − | − | − | − | − |
| 20 | + | + | + | − | + | + | − | + | + | − | + | + | − | − | − | − | − | − |
| 25 | − | − | − | − | − | − | − | − | − | − | − | − | − | − | − | − | − | − |

Note:
In Table 3, the symbols "+" and "−" mean "crystallized" and "not crystallized", respectively.

TABLE 4

| Composition (part by Weight) | | | | | | | | | | | | | |
|---|---|---|---|---|---|---|---|---|---|---|---|---|---|
| | Water | 17.5 | 23 | 30 | 37 | 46 | 57 | 17.5 | 23 | 30 | 37 | 46 | 57 |
| | (water content (%) with respect to syrup) | (43) | (50) | (56) | (61) | (68) | (71) | (20) | (25) | (30) | (35) | (40) | (45) |
| | Trehalose | 23.2 | 23.2 | 23.2 | 23.2 | 23.2 | 23.2 | 23.2 | 23.2 | 23.2 | 23.2 | 23.2 | 23.2 |
| | (trehalose content (%) with respect to syrup) | (57) | (50) | (44) | (39) | (34) | (29) | (27) | (25) | (23) | (22) | (20) | (18) |
| | Glucose | 0 | 0 | 0 | 0 | 0 | 0 | 10 | 10 | 10 | 10 | 10 | 10 |
| | Maltose | 0 | 0 | 0 | 0 | 0 | 0 | 16.8 | 16.8 | 16.8 | 16.8 | 16.8 | 16.8 |
| | Maltitol | 0 | 0 | 0 | 0 | 0 | 0 | 10 | 10 | 10 | 10 | 10 | 10 |
| | Sucrose | 0 | 0 | 0 | 0 | 0 | 0 | 10 | 10 | 10 | 10 | 10 | 10 |
| Bacterial contamination | | + | + | + | + | + | + | − | − | − | − | + | + |
| Crystallization | | + | + | + | + | − | − | + | − | − | − | − | − |
| Judgement | | | | Control | | | | Control | | Present invention | | Control | |

Note:
In Table 4, the symbols "+" and "−" mean "crystallized" and "not crystallized", respectively.

As is evident from the results in Table 4, it was revealed that the present high trehalose content syrups with a water content of 25–35 w/w % are free of bacterial contamination, and those with a trehalose content of 25 w/w % or lower are free of crystallization. The facts indicate that the present syrups are stable even when stored at ambient temperature.

The followings are the preferred examples of the present invention. Examples A and B explain the present high trehalose content syrups and the compositions prepared therewith:

EXAMPLE A-1

One part by weight of a 50 w/w % aqueous trehalose solution, prepared by dissolving trehalose in water under heating conditions, was mixed to homogeneity with 1.5 parts by weight of a starch syrup saccharified with an acid, having a DE 43 and an about 20 w/w % water, as a crystallization inhibitory agent for trehalose, to obtain a high trehalose content syrup with a DE of about 30, containing about 20 w/w % trehalose, about 32 w/w % water, and other saccharides. The product is stable and readily handleable even at ambient temperature and can be suitably used as a sweetener, taste-improving agent, and quality-improving agent in compositions such as food products, cosmetics and pharmaceuticals.

EXAMPLE A-2

Corn starch was prepared into a 30 w/w % starch suspension which was then treated with α-amylase to obtain a liquefied solution with a DE 4. The liquefied solution was mixed with 500 units/g starch of isoamylase, 10 units/g starch of a trehalose-releasing enzyme, and 5 units/g starch of a non-reducing saccharide-forming enzyme as disclosed in Japanese Patent Application No.79,291/94, and allowed to react at pH 6.0 and 40° C. for 48 hours. The reaction mixture was heated to inactivate the remaining enzyme, decolored in a conventional manner, desalted, purified and concentrated into an about 55 w/w % syrup containing about 76 w/w % trehalose, d.s.b. One part by weight of the syrup was mixed to homogeneity with one part by weight of "MALT-RUP®", a high maltose content syrup with an about 20 w/w % water commercialized by Hayashibara Shoji, Inc., Okayama, Japan, as a crystallization inhibitory agent for trehalose, to obtain a high trehalose content syrup with a DE of about 29, containing about 21 w/w % trehalose, about 33 w/w % water, and other saccharides. The product is stable and readily handleable even at ambient temperature and can be suitably used as a sweetener, taste-improving agent, and quality-improving agent in compositions such as food products, cosmetics and pharmaceuticals.

EXAMPLE A-3

An about 55 w/w % trehalose syrup which contains about 76 w/w % trehalose, obtained by the method in Example A-2, was placed in a crystallizer, mixed with one w/w % hydrous crystalline trehalose as a seed, and cooled while stirring. The resulting massecuite was separated and washed by spraying with cold water, followed by collecting a mother liquor and a high purity hydrous crystalline trehalose. The mother liquor contained about 46 w/w % trehalose, d.s.b., and about 32 w/w % water. Two parts by weight of the mother liquor was mixed to homogeneity with one part by weight of "TETRUP®", a high maltotetraose content syrup with a water content of about 28 w/w %, commercialized by Hayashibara Shoji, Inc., Okayama, Japan, to obtain a high trehalose content syrup with a DE of about 27, containing about 21 w/w % trehalose, about 31 w/w % water, and other saccharides. The product is satisfactorily stable and readily handleable even at ambient temperature, and can be suitably used as a sweetener, taste-improving agent, and quality-improving agent in compositions such as food products, cosmetics and pharmaceuticals.

EXAMPLE A-4

Two parts by weight of a mother liquor containing about 46 w/w % trehalose, d.s.b., and about 32 w/w % water obtained by the method in Example A-3 was mixed to homogeneity with one part by weight of "PANORUP®", a high panose content syrup with a water content of about 25 w/w %, as a crystallization inhibitory agent for trehalose, to obtain a high trehalose content syrup with a DE of about 37, containing about 21 w/w % trehalose, about 30 w/w % water, and other saccharides. The product is stable and readily handleable even at ambient temperature and can be used as a sweetener, taste-improving agent, quality-improving agent, low-cariogenic sweetener, growth-promoting agent for bifid bacteria, and calcium absorption-promoting agent in compositions such as food products, cosmetics and pharmaceuticals.

EXAMPLE A-5

Two parts by weight of a mother liquor containing about 46 w/w % trehalose, d.s.b., and about 32 w/w % water obtained by the method in Example A-3 was mixed to homogeneity with one part by weight of "COUPLING SUGAR®", a glycosyl sucrose syrup with a water content of about 25 w/w %, as a crystallization inhibitory agent for trehalose, to obtain a high trehalose content syrup with a DE of about 24, containing about 21 w/w % trehalose, about 30 w/w % water, and other saccharides. The product is stable and readily handleable at ambient temperature and can be used as a sweetener, taste-promoting agent, quality-improving agent, and low-cariogenic sweetener in compositions such as food products, cosmetics and pharmaceuticals.

EXAMPLE A-6

Two parts by weight of a mother liquor containing about 46 w/w % trehalose, d.s.b., and about 32 w/w % water obtained by the method in Example A-3 was mixed to homogeneity with one part by weight of "NYUKA OLIGO®", a high lactosucrose content syrup with a water content of about 28 w/w %, commercialized by Hayashibara Shoji, Inc., Okayama, Japan, as a crystallization inhibitory agent for trehalose, to obtain a high trehalose content syrup with a DE of about 27, containing about 21 w/w % trehalose, about 31 w/w % water, and other saccharides. The product is stable and readily handleable at ambient temperature and can be used as a growth-promoting agent for bifid bacteria, and calcium absorption-promoting agent in compositions such as food products, cosmetics and pharmaceuticals.

EXAMPLE A-7

A high trehalose content syrup obtained by the method in Example A-2 was placed in an autoclave, mixed with 10 w/w % Raney Nickel, and heated to 90°–120° C. while stirring, followed by increasing the hydrogen pressure to 20–120 kg/cm$^2$ to complete the hydrogenation and removing the Raney Nickel. Thereafter, the resulting mixture was in a conventional manner decolored, desalted, purified and concentrated into a high trehalose content syrup with a DE of less than 1.0, containing about 21 w/w % trehalose, about 30 w/w % water, and other non-reducing saccharides.

The product is substantially free from reducibility, satisfactorily stable and readily handleable, and can be suitably used as a sweetener, taste-improving agent, quality-improving agent, low-cariogenic sweetener, and low-caloric sweetener in compositions such as food products, cosmetics and pharmaceuticals.

EXAMPLE A-8

Corn starch was prepared into a 30 w/w % starch suspension which was then treated with α-amylase to obtain a liquefied solution with a DE 15. To the liquefied solution were added 5 units/g starch of a non-reducing saccharide-forming enzyme as disclosed in Japanese Patent Application No.79,291/94, 10 units/g starch of a trehalose-releasing enzyme, and 50 units/g starch of isoamylase, followed by an enzymatic reaction at pH 6.0 and 40° C. for 24 hours. Thereafter, the reaction mixture was mixed with 10 units/g β-amylase, allowed to react for 10 hours, heated to inactivate the remaining enzyme, and in a conventional manner decolored, desalted, purified and concentrated to obtain a high trehalose content syrup with a DE of about 38, containing about 22 w/w % trehalose, about 30 w/w % water, and other saccharides. The product is stable and readily handleable even at ambient temperature and can be suitably used as a sweetener, taste-improving agent, and quality-improving agent in compositions such as food products, cosmetics and pharmaceuticals.

EXAMPLE A-9

"MALSTAR®", a high maltose content syrup commercialized by Hayashibara Shoji, Inc., Okayama, Japan, was mixed with water to obtain an about 40 w/w % solution which was then mixed with 2 units/g maltose of a maltose/trehalose converting enzyme disclosed in Japanese Patent Application No.144,092/94 and subjected to an enzymatic reaction at 35° C. and pH 7.0 for 16 hours. According to a conventional manner, the reaction mixture was heated to inactivate the remaining enzyme, decolored, desalted, purified and concentrated to obtain a high trehalose content syrup with a DE 42, containing about 20 w/w % trehalose, about 30 w/w % water, and other saccharides. The product is stable and readily handleable even at ambient temperature and can be suitably used as a sweetener, taste-improving agent and quality-improving agent in compositions such as food products, cosmetics and pharmaceuticals.

EXAMPLE A-10

A high trehalose content syrup obtained by the method in Example A-9 was hydrogenated by the method in Example A-7, and the hydrogenated product was purified and concentrated to obtain a high trehalose content syrup with a DE of less than 1.0, containing about 20 w/w % trehalose, about 30 w/w % water, and other non-reducing saccharides. The product is substantially free from reducibility, satisfactorily stable, and readily handleable, and can be suitably used as a sweetener, taste-improving agent, quality-improving agent, low-cariogenic sweetener, and low-caloric sweetener in compositions such as food products, cosmetics and pharmaceuticals.

EXAMPLE B-1

Lactic Acid Beverage

One hundred and seventy-five parts by weight of skim milk powder and 150 parts by weight of a high trehalose content syrup, obtained by the method in Example A-6, were dissolved in 1,200 parts by weight of water. The resulting solution was sterilized by heating at 65° C. for 30 min, cooled to 40° C., and inoculated with 30 parts by weight of laotic acid bacteria as a starter, followed by the fermentation at 37° C. for 8 hours to obtain a lactic acid beverage. The product, which has a satisfactory flavor and contains oligosaccharides and stabilized lactic acid bacteria, promotes the growth of bifid bacteria.

EXAMPLE B-2

Coffee

About 100 parts by weight of a roasted coffee was powdered and extracted with about 1,000 parts by weight of hot water to obtain an about 860 parts by weight of a coffee extract. About 450 parts by weight of the extract was mixed to homogeneity with about 150 parts by weight of a high trehalose content syrup obtained by the method in Example A-7, and about 400 parts by weight of water containing an adequate amount of sodium bicarbonate to obtain a coffee with a pH of about 7. The coffee was in a conventional manner canned and sterilized at 120° C. for 30 min. The product has a satisfactory flavor and taste. When stored in an automatic coffee vending machine at 60° C. for one month, the product retains the original flavor and taste. The product also retains the quality even when cooled before testing in summer season.

EXAMPLE B-3

Hard Candy

One hundred parts by weight of a high trehalose content syrup obtained by the method in Example A-6 was concentrated in vacuo by heating up to give a moisture content of less than 2 w/w %. The concentrate was mixed with 0.5 parts by weight of citric acid and adequate amounts of a lemon flavor and a coloring agent, and the mixture was formed in a conventional manner to obtain a hard candy. The product has a satisfactory biting property and taste and is substantially free from crystallization of saccharides and change of shape.

EXAMPLE B-4

An (Beam Jam)

Ten parts by weight of adzuki beans as a material was mixed and boiled with water in a conventional manner, followed by removing the astringency, harshness and watersoluble impurities to obtain an about 21 parts by weight of an adzuki-tsubu-an (boiled adzuki beans which retain their shape). The product was mixed with 14 parts by weight of sucrose, 5 parts by weight of a high trehalose content syrup obtained by the method in Example A-7, and 4 parts by weight of water, and the mixture was boiled, further mixed with a small amount of a salad oil, and kneaded up while retaining the shape of adzuki beans to obtain an about 35 parts by weight of an "an". The product, which is free from fading of color and has a satisfactory biting property, flavor and taste, can be suitably used as a material for bean-jam buns, buns with beam-jam fillings, dumplings, bean-jam-filled waters, ice creams, and sherbets.

EXAMPLE B-5

Strawberry Jam

Fifteen parts by weight of fresh strawberry, 6 parts by weight of sucrose, 2 parts by weight of maltose, 4 parts by weight of a high trehalose content syrup obtained by the method in Example A-1, 0.05 parts by weight of pectin, and 0.01 part by weight of citric acid were mixed and boiled up to obtain a strawberry jam which was then canned. The product is a high quality jam with a satisfactory flavor and color.

EXAMPLE B-6

Bun

One hundred parts by weight of wheat flour, 2 parts by weight of a yeast, 5 parts by weight of sucrose, 2 parts by weight of a high trehalose content syrup obtained by the method in Example A-8, and 0.1 part by weight of a yeast food were kneaded with water, followed by the fermentation at 26° C. for 2 hours. The fermented product was aged for 30 min and baked. The product burnt brown is soft and full and has a satisfactory texture, color and sweetness.

EXAMPLE B-7

Custard Cream

One hundred parts by weight of corn starch, 100 parts by weight of a high trehalose content syrup obtained by the method in Example A-9, 80 parts by weight of maltose, 20 parts by weight of sucrose, and one part by weight of salt were sufficiently mixed, and further admixed with 280 parts by weight of fresh eggs, gradually admixed with 1,000 parts by weight of boiling milk, and heated while stirring. The heating was terminated when the whole contents were completely gelatinized to show semi-transparency, then cooled, admixed with an adequate amount of a vanilla flavor, weighed, injected and wrapped to obtain a custard cream. The product has a smooth gloss and mild sweetness and taste. The retrogradation of the gelatinized starch was well prevented, and this gives the product a relatively long shelf-life.

EXAMPLE B-8

Gyuhi (Starch Paste)

Four parts by weight of a glutinous rice powder was dissolved in 6 parts by weight of water, and the suspension was put in a crate spread with a wet cloth, steamed at 100° C. for 20 min and sufficiently mixed with 2 parts by weight of sugar and 6 parts by weight of a high trehalose content syrup obtained by the method in Example A-3. The mixture was formed into a gyuhi. The product has a satisfactory flavor and taste. The retrogradation of the gelatinized starch was well prevented, and this gives the product a relatively long shelf-life.

EXAMPLE B-9

Icing

Eighty parts by weight of a high trehalose content syrup, obtained by the method in Example A-2, was mixed with 1.2 parts by weight of sugar esther as an emulsifier under heating conditions, and the mixture was mixed with 107 parts by weight of "TREHAOSE", a hydrous crystalline trehalose commercialized by Hayashibara Shoji, Inc., Okayama, Japan, and further mixed with 7.5 parts by weight of oil and fat while keeping at 45° C. to obtain an icing.

The product, containing a fine trehalose crystal, has a satisfactory moldability without stickiness and an insubstantial quality deterioration.

EXAMPLE B-10

Soft Candy

Sixty parts by weight of a high trehalose content syrup, obtained by the method in Example A-4, was mixed with 180 parts by weight of "TREHAOSE", a hydrous crystalline trehalose commercialized by Hayashibara Shoji, Inc., Okayama, Japan, and the mixture was concentrated by heating and mixed with 15 parts by weight of 20% pullulan solution and 60 parts by weight of 10% agar solution, followed by the concentration under heating conditions similarly as above. The concentrate was mixed with 70 parts by weight of milk cream, 120 parts by weight of skim milk powder, 1.5 parts by weight of sugar ester, and 40 parts by weight of margarine, and concentrated by heating up to give a brix degree of 85, followed by shaping the concentrate in conventional manner into a soft candy.

The product contains a fine trehalose crystal, has a satisfactory milk flavor, and does not stick to your teeth. The product is a healthy candy without fear of causing dental carries because it does not contain sugar.

EXAMPLE B-11

Candy for Cachou

Fifteen parts by weight of a high trehalose content syrup, obtained by the method in Example A-3, was mixed with 285 parts by weight of "TREHAOSE", a hydrous crystalline trehalose commercialized by Hayashibara Shoji, Inc., Okayama, Japan, 5 parts by weight of pullulan, and 100 parts by weight of water, and the mixture was heated, concentrated at 112° C., mixed with 4 parts by weight of alcohol solution of 15% l-menthol, and shaped in conventional manner to obtain a desired product.

The product, containing a fine trehalose crystal, is substantially free of quality deterioration for a relatively long period of time.

EXAMPLE B-12

Bonbon

Five parts by weight of a high trehalose content syrup, obtained by the method in Example A-7, was mixed with 300 parts by weight of "TREHAOSE", a hydrous crystalline trehalose commercialized by Hayashibara Shoji, Inc., Okayama, Japan, 115 parts by weight of water, and the mixture was concentrated by heating up to give a brix degree of 70 and cooled to 80° C, then mixed with 40 parts by weight of a brandy, followed by shaping the mixture into a desired product.

The product has a satisfactory flavor and is free of quality deterioration for a relatively long period of time.

EXAMPLE B-13

Ham

Fifteen parts by weight of salt and 3 parts by weight of potassium nitrate were added to homogeneity to 1,000 parts by weight of sliced hams which were then piled up and stored overnight in a cool place. Thereafter, the hams were soaked in a solution consisting of 440 parts by weight of water, 100 parts by weight of salt, 3 parts by weight of potassium nitrate, 60 parts by weight of a high trehalose content syrup obtained by the method in Example A-10, and an adequate amount of a spice for 7 days in a cool place. The resulting hams were in a conventional manner washed with cold water, tied up, smoked, cooked, cooled and packed to obtain the desired hams. The hams have a satisfactory color, flavor, taste and quality.

EXAMPLE B-14

Tsukudani (Food boiled down in soy)

To 250 parts by weight of tangle, which had been removed impurities, treated with acid and cut into cubes, were added 212 parts by weight of tangle, which had been removed impurities, treated with acid and cut into cubes, were added 212 parts by weight of soy, 318 parts by weight of an amino acid solution, 70 parts by weight of a high trehalose content syrup obtained by the method in Example A-4, and 20 parts by weight of sucrose. The mixture was admixed with 12 parts by weight of sodium glutamate and 8 parts by weight of caramel, and boiled up to obtain a tsukudani of tangle. The product has a relatively low cariogenicity and a satisfactory taste, flavor, color and gloss, and it would stimulate one's appetite.

EXAMPLE B-15

Cosmetic Cream

Two parts by weight of polyoxyethylene glycol monostearate, 5 parts by weight of glyceryl monostearate, selfemulsifying, 2 parts by weight of a high trehalose content syrup obtained by the method in Example A-5, one part by weight of α-glycosyl rutin, one part by weight of liquid paraffine, 10 part by weight of glyceryl tri(2-ethylhexanoate), and an adequate amount of an antiseptic were dissolved by heating in a conventional manner. The mixture was admixed with 2 parts by weight of L-lactic acid, 5 parts by weight of 1,3-butylene glycol, 66 parts by weight of refined water, and the resulting mixture was emulsified by a homogenizer, admixed with an adequate amount of a flavor, and mixed by stirring to obtain a cream. The product, with a satisfactory tolerance to oxidation and a relatively high stability, can be suitably used as a high quality sunburn, skin-beautifying agent and skin-whitening agent.

EXAMPLE B-16

Tooth Paste

A tooth paste was obtained by mixing the composition below in a conventional manner. The product has an adequate sweetness suitable for children.

| Composition | |
|---|---|
| Potassium secondary phosphate | 45.0 parts by weight |
| Pullulan | 2.95 parts by weight |
| Sodium lauryl sulfate | 1.5 parts by weight |
| Glycerine | 20.0 parts by weight |
| Polyoxyethylene sorbitan laurate | 0.5 parts by weight |
| Antiseptic | 0.05 parts by weight |
| A high trehalose content syrup obtained by the method in Example A-10 | 12.0 parts by weight |

-continued

| Composition | |
|---|---|
| Maltitol | 5.0 parts by weight |
| Water | 13.0 parts by weight |

EXAMPLE B-17

Ointment for Trauma

Two hundred parts by weight of a high trehalose content syrup obtained by the method in Example A-2 and 360 parts by weight of maltose were admixed with 3 parts by weight of iodine dissolved in 50 parts by weight of methanol, and further mixed with 140 parts by weight of a 14 w/v % aqueous pullulan solution to obtain an ointment for trauma, with an adequate spreadability and adhesiveness. The iodine in the product exerts a bactericidal activity, and the trehalose and maltose in the product act as energy-supplementing agents for living cells, and therefore the product cures wounded sites in a shortened period of time.

As is described above, the present invention provides a high trehalose content syrup which is stable, free of or substantially free of crystallization, and substantially free of bacterial contamination even at ambient temperature. Unlike conventional crystalline trehalose powders, the present syrup does not require a dissolving step and is readily handleable, stored in tanks, and transported by pumps and tank trucks. Compared with conventional starch sugars, the present syrup is a novel type of syrup with a lower DE and viscosity and a higher sweetening power, and it can be advantageously used as a sweetener, taste-improving agent or quality-improving agent in the production of food products, cosmetics and pharmaceuticals. The present invention provides a high trehalose content syrup with a satisfactory stability even at ambient temperature, which has long been expected but could have never been realized. Thus, the present invention gives an outstanding influence on the food, cosmetic and pharmaceutical industries.

While there has been described what is at present considered to be the preferred embodiments of the invention, it will be understood the various modifications may be made therein, and it is intended to cover in the appended claim s all such modifications as fall within the true spirit and scope of the invention.

We claim:

1. A supersaturated trehalose syrup in which trehalose is dissolved at ambient temperature in an amount that exceeds the saturation concentration of trehalose in water and in which one or more other saccharides coexist with trehalose in said syrup in an amount at least as much as the amount of trehalose, said syrup being isolated and substantially free from crystallization and bacterial contamination even at ambient temperature.

2. The supersaturated trehalose syrup of claim 1, which contains 18.5–25.0 w/w % of said trehalose, 40.0–56.5 w/w % of said other saccharide(s), and 25.0–35.0 w/w % water based on 100 weight % with respect to the syrup.

3. The supersaturated trehalose syrup of claim 1, wherein said other saccharide(s) is selected from one or more members of the group consisting of reducing monosaccharides, non-reducing monosaccharides, and oligosaccharides.

4. The supersaturated trehalose syrup of claim 1, wherein said other saccharide(s) are two or more members selected from the group consisting of reducing saccharides and non-reducing saccharides having no more than five monosaccharide units.

5. The supersaturated trehalose syrup of claim 1, which is a sweetener free of crystallization at 10° C.

6. A composition prepared by incorporating at least 0.5 w/w % of supersaturated trehalose syrup of claim 1 as part of the composition.

7. The composition of claim 6, wherein said supersaturated trehalose syrup comprises 18.5–25.0 w/w % trehalose, 40.0–56.5 w/w % of said other saccharide(s), and 25.0–35.0 w/w % water.

8. The composition of claim 6, wherein said other saccharide(s) is selected from one or more members of the group consisting of reducing monosaccharides, non-reducing saccharides, and oligosaccharides.

9. The composition of claim 6, wherein said supersaturated trehalose syrup is free of crystallization at 10° C.

10. The composition of claim 6, which is a food product, a cosmetic or a pharmaceutical.

11. A method for preventing the crystallization of a high trehalose content syrup, which comprises dissolving trehalose in water in an amount that exceeds its saturation concentration while dissolving other saccharide(s) in the water in an amount which is at least as much as the amount of said trehalose being dissolved.

12. The method of claim 11, wherein said syrup comprises 18.5–25.0 w/w % of said trehalose, 40.0–56.5 w/w % of said other saccharide, and 25.0–35.0 w/w % of water based on 100 weight % with respect to the syrup.

13. The method of claim 11, wherein said other saccharide (s) is selected from one or more members of the group consisting of reducing monosaccharides, non-reducing saccharides, and oligosaccharides.

14. A method for preventing the crystallization of trehalose in a supersaturated trehalose syrup, which comprises the step of dissolving an agent for preventing the crystallization of trehalose in a supersaturated trehalose syrup, wherein said agent contains an effective ingredient selected from one or more members of the group consisting of reducing monosaccharides, non-reducing saccharides, and oligosaccharides in an amount at least as much as the amount of trehalose in said syrup.

15. The method of claim 14, wherein said agent is selected from two or more members of the group consisting of reducing saccharides and non-reducing saccharides having no more than five monosaccharide units.

16. The method of claim 14, wherein said supersaturated trehalose syrup contains 25–35 w/w % water.

* * * * *